United States Patent
Ng

(10) Patent No.: US 11,623,087 B1
(45) Date of Patent: Apr. 11, 2023

(54) METHOD FOR NON-SURGICAL CORRECTION OF JOINT DEFORMITY

(71) Applicant: Milly Ng, Hong Kong (HK)

(72) Inventor: Milly Ng, Hong Kong (HK)

( * ) Notice: Subject to any disclaimer, the term of this patent is extended or adjusted under 35 U.S.C. 154(b) by 410 days.

(21) Appl. No.: 16/529,412

(22) Filed: Aug. 1, 2019

(51) Int. Cl.
*A61N 1/36* (2006.01)
*A61H 7/00* (2006.01)

(52) U.S. Cl.
CPC ........ *A61N 1/36014* (2013.01); *A61H 7/003* (2013.01); *A61H 2201/10* (2013.01)

(58) Field of Classification Search
CPC . A61N 1/36014; A61H 7/003; A61H 2201/10
See application file for complete search history.

(56) References Cited

U.S. PATENT DOCUMENTS

| 5,397,338 A * | 3/1995 | Grey | A61N 1/36021 607/115 |
| 5,800,458 A * | 9/1998 | Wingrove | A61N 1/3603 607/2 |
| 2008/0287859 A1* | 11/2008 | Miller | A61B 17/3472 604/21 |
| 2016/0361539 A1* | 12/2016 | Nathanson | A61N 1/0452 |
| 2017/0266446 A1* | 9/2017 | O'Clock | A61N 1/36014 |

\* cited by examiner

*Primary Examiner* — Gary Jackson
*Assistant Examiner* — Sebastian X Lukjan
(74) *Attorney, Agent, or Firm* — Leavitt Eldredge Law Firm

(57) ABSTRACT

A method of non-surgical correction of joint deformity using a therapy stimulator machine that includes a first and second handheld probe electrode; using the hand held probe electrodes with water to apply pressure to locations and wiggle the probe electrodes around the joint to stimulate directing toxic waste to the blood circulatory system of the patient.

6 Claims, 3 Drawing Sheets

METHOD FOR NON-SURGICAL CORRECTION OF JOINT DEFORMITY

BACKGROUND

1. Field of the Invention

The present invention relates generally to methods for correction of joint deformity, and more specifically to a non-surgical method not using medication to correct joint deformity in patients.

2. Description of Related Art

Methods for joint correction are common in the art and typically require surgical procedures. Common joint deformities include scoliosis and kyphosis of the spine, hip deformities, knee deformities, and big toe deformities. Surgical procedures are inherently risky, can be expensive, and require extensive recovery periods. Further, these procedures are not always effective to treat the problem. Accordingly, it is an object of the present invention to provide a non-surgical method to aid in correction of joint deformity.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
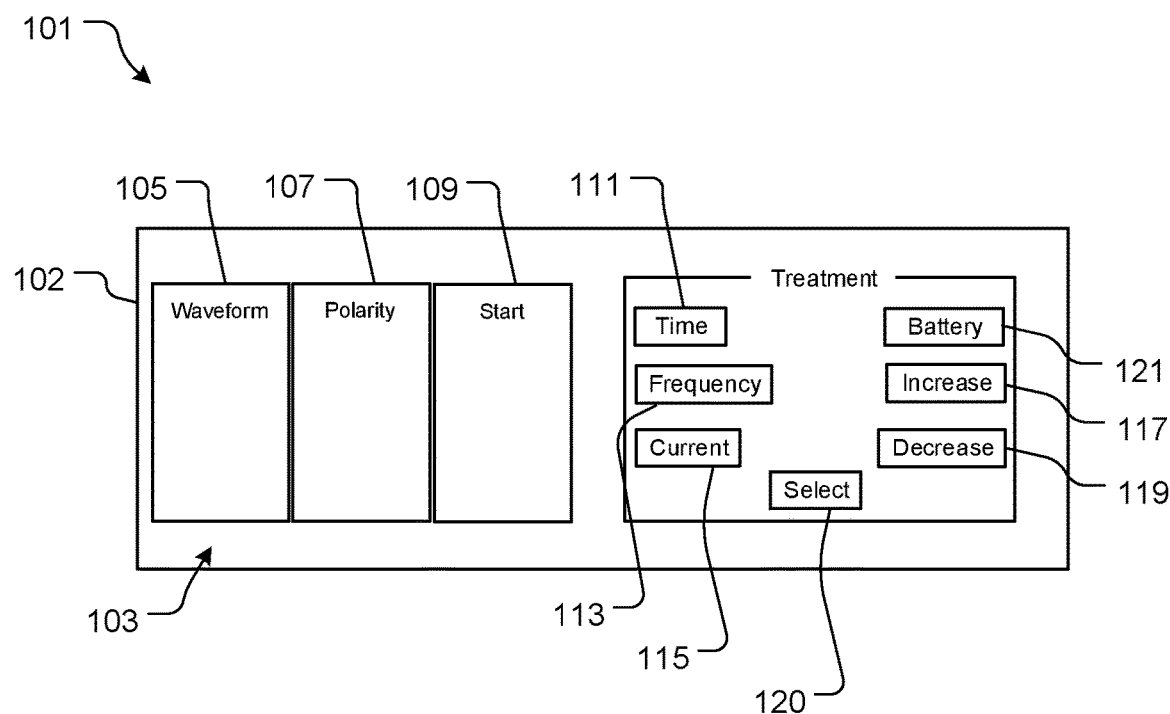
FIG. 1 is a front view of a therapy stimulator machine in accordance with the present invention.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional methods of joint deformity correction. Specifically, the present invention provides for a minimal pain and recovery period procedure that is effective in correcting joint deformity. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
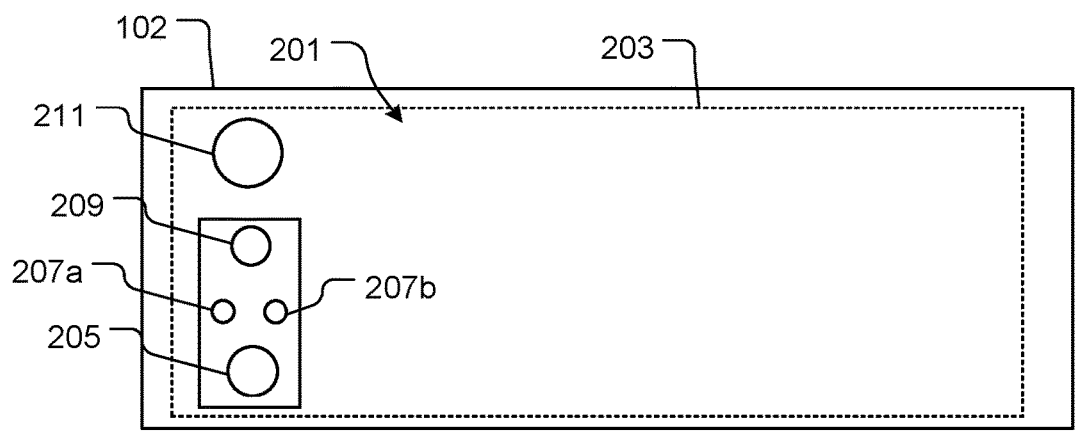
FIG. 2 is a back view of the machine of FIG. 1.

Referring now to the drawings wherein like reference characters identify corresponding or similar elements throughout the several views, FIGS. 1-2 depicts front and back views of a therapy stimulator machine 101 for use in accordance with the present invention.

In the present invention, the machine 101 is used during a method and procedure, as will be discussed herein. It should be appreciated that the machine can vary, however, the machine discussed is the preferred embodiment.

The machine 101 includes a housing 102 with a front panel 103 that can include a plurality of controls that allow for the user to set the machine to desired settings. As shown, the settings can include a waveform selection 105, a polarity selection 107, and a start/activation button 109. In addition, the user can select needed treatment elements, such as a treatment time 111, a desired frequency 113, and a current selection 115. The user will utilize the controls including increase 117, decrease 119, and select 120 to set the treatment. For example, the user can select a treatment time of 20 minutes, at a frequency of 0.3 Hz. Upon activation of the start button, the treatment will start at the desired frequency for the desired time.

As shown, the panel can further include a battery indicator 121 to indicate a level of battery charge. In the preferred embodiment, the battery 203 is a rechargeable battery.

As shown in FIG. 2, the housing 102 can further include a back panel 201, wherein the back panel includes a plurality of ports and other elements. As shown, such elements can include a jack 205 for connecting the hand held probe electrodes, a jack 207a-b for using adhesive pads, a knob 209 for adjusting audio volume, and a speaker 211, wherein the speaker can indicate that the time is up or the like.

Figure 3:
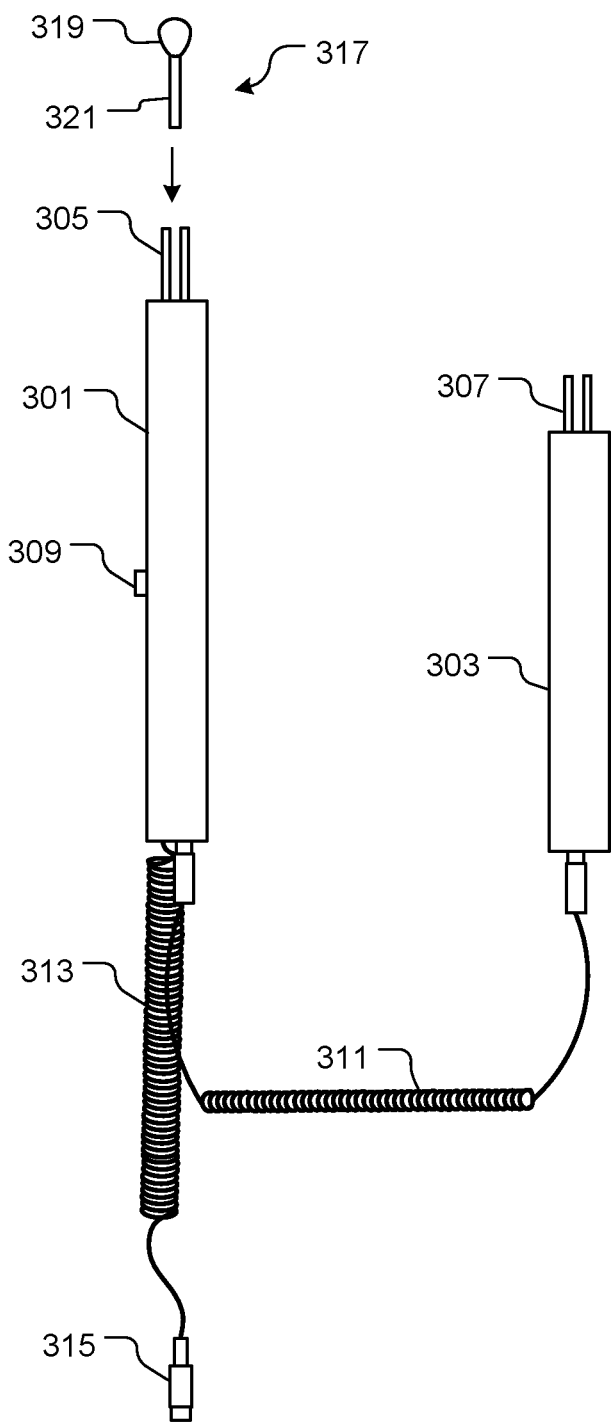
FIG. 3 is a top view of a first and second hand held probe electrode in accordance with the present invention.

In FIG. 3, a first and second hand held probe electrodes 301, 303 are shown. It should be appreciated that in the preferred embodiment, the electrodes 301, 303 include dual Q probe electrodes 305, 307 composed of stainless steel, and the first electrode 301 can include an on/off button 309 configured to activate and deactivate the electrodes. The first and second electrodes 301, 303 are electrically connected via a coiled wire banana plug 311 and an extensible coiled wire 313 is connected to the first electrode 301 and includes a connector 315 for engaging with the jack 205 of the housing. It should be appreciated that the probe electrodes connect to the housing for power and activation of electro stimulation.

In the preferred embodiment, a cotton swab 317 is cut in half and wet with water, such that the cotton bud 319 is saturated. The shaft 321 of the cotton swab 317 can then be inserted into the electrodes 305 such that the water is in communication with the metal, thereby allowing for conductivity.

It should be appreciated that one of the unique features believed characteristic of the present application is the use of machine 101 in connection with the first and second probe electrodes to provide pressure to a plurality of locations associated with a patient's joint, wherein the application of pressure and stimulation directs toxic waste products that has built up in and around the joint over the years to be carried away through the blood circulation, so can be discarded out of the body, hence providing both in pain relief and mobility.

Figure 4:
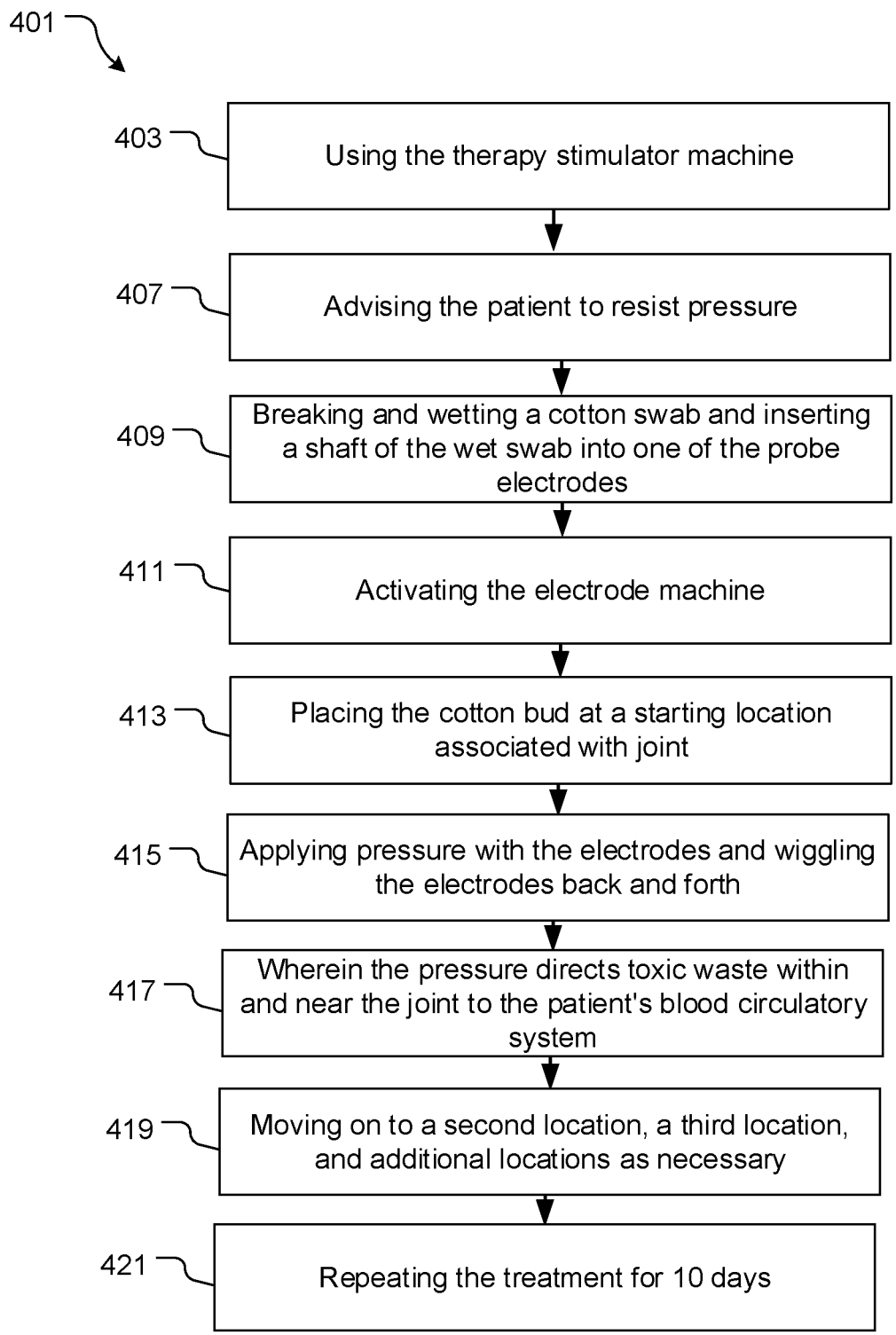
FIG. 4 is a flowchart of the method of use associated with non-surgical joint deformity correction in accordance with the present invention.

In FIG. 4, a flowchart 401 depicts a method of non-surgical correction of joint deformity. During use, the therapy stimulator machine with the first and second hand held probe electrodes is used, as shown with box 403. In the event that a patient suffers from scoliosis, the S curve of the spine is caused by muscle imbalance, one side is strong while the other side is weaker. In addition to the soft tissue imbalance, most of the deformed joints also have deposits or osteophytes or body overgrowth that the limited mobility of the joint or set the joint into deformity. Hence, the practitioner must have sound knowledge of Anatomy and Kinesiology for successful treatment.

In order to get the maximum effect of joint correction, the practitioner will instruct the patient to put the muscle under treatment in the most lengthened position then resist the action of that particular muscle either actively or passively, to prepare for the practitioner to work along the muscle fibers covering all related muscles of the joint deformity, as shown with box 407.

A cotton swab is broken in half and wet, such that the cotton bud is wet, and the shaft is inserted into the first hand held probe electrode, thereby putting water in electrical communication with the probes, as shown with box 409. The user will activate the machine, either through use of the button on the probe or through the activation button on the housing, as shown with box 411. The cotton bud is then placed on a starting point about a patient's joint, as shown with box 413. The user will apply pressure and wiggle the electrodes back and forth, and then move in approximately 1 cm increments onto the next location, as shown with box 415. In the preferred treatment, the practitioner will move in approximately 1 inch increments along the joint.

It should be appreciated that the pressure applied should aim to be treated, i.e. if superficial, then lighter pressure with 2 electrodes together; if as deep as in the middle of the hip joint, then one should use a through and through technique placing the electrodes on the opposite side of the joint, the frequency should preferably be at 0.3 Hz, wherein the pressure stimulates toxin removal from around the joint, as shown with box 417. The practitioner can then move on to the second, third, fourth, etc. locations, as shown with box 419. It should be appreciated that in the preferred embodiment, the procedure is repeated for 10 days on a daily basis for best results, as shown with box 421.

It should further be appreciated that in some procedures, the patient should sign an agreement that they acknowledge the continuity of the treatment and the sensation during the treatment. The patient must complete all 10 days of the procedure and comply with the rules of drinking 2-3 liters of water, refraining from caffeine, alcohol, and smoking.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method of non-surgical correction of joint deformity, comprising:
   providing a therapy stimulator machine having:
      a housing having a front panel and a back panel, the housing having a rechargeable battery inside, the housing having a start button;
      a first hand held probe electrode connected to a second hand held probe electrode via a banana plug, the first hand held probe electrode having:
      an on/off switch;
      a first probe secured to the first hand held probe, the first probe is configured to removably attach to a first cotton swab;
      a second probe secured to the second hand held probe, the second probe is configured to removably attach to a second cotton swab;
   a cord attached to the first hand held probe electrode and plugged into the housing;
   a frequency selection button configured to allow a user to select a desired frequency;
      selecting a joint of the patient, the joint having a medical deformation;
      breaking the first cotton swab such that the cotton swab has a shaft and cotton bud;
      wetting the cotton bud of the cotton swab;
      inserting the shaft of the first cotton swab into the first hand held probe electrode such that water will come into contact with metal of the first hand held probe electrode;
      activating the electrode machine through the start button;
      adjusting the desired frequency to 0.38 Hertz for a duration of 20 minutes;
      placing the cotton bud at a starting point associated with the joint;
      applying pressure and a desired microcurrent to the starting point through the cotton bud, wherein electrostimulation is created by both the desired frequency and microcurrent via the therapy stimulator machine; and
      directing the patient to resist the pressure;
      wherein the application of pressure to the starting point directs toxic waste to the patient's blood circulatory system to correct joint deformity.

2. The method of claim 1, wherein the therapy stimulator machine further includes:
   a waveform selection;
   a polarity selection;
   a time selection;
   a current selection; and
   a battery indicator.

3. The method of claim 1, further comprising:
   repeating the treatment daily for ten days.

4. The method of claim 1, further comprising:
   moving the cotton bud to a second location along the joint; and
   applying pressure to the second location.

5. The method of claim 4, further comprising:
   moving the cotton bud to a third location associated with the joint; and
   applying pressure to the third location.

6. The method of claim 1, further comprising:
   applying pressure to the starting point with the first hand held probe electrode and the second hand held probe electrode; and
   wiggling the first hand held probe electrode and the second hand held probe electrode back and forth.

\* \* \* \* \*